(12) United States Patent
Suzuki

(10) Patent No.: US 7,158,836 B2
(45) Date of Patent: Jan. 2, 2007

(54) ELECTRODE MEMBER FOR RETINAL STIMULATION, AND ARTIFICIAL RETINAL DEVICE USING THE ELECTRODE MEMBER

(76) Inventor: Satoshi Suzuki, 17-1-101, Mikannyama-Cho, Mizuho-Ku, Nagoya-Shi, Aichi-Prefecture (JP) 467-0041

( * ) Notice: Subject to any disclaimer, the term of this patent is extended or adjusted under 35 U.S.C. 154(b) by 398 days.

(21) Appl. No.: 10/469,559

(22) PCT Filed: Feb. 15, 2002

(86) PCT No.: PCT/JP02/01340

§ 371 (c)(1),
(2), (4) Date: Aug. 29, 2003

(87) PCT Pub. No.: WO02/080816

PCT Pub. Date: Oct. 17, 2002

(65) Prior Publication Data

US 2004/0078064 A1 Apr. 22, 2004

(30) Foreign Application Priority Data

Mar. 30, 2001 (JP) ............................. 2001-101483

(51) Int. Cl.
*A61N 1/05* (2006.01)
(52) U.S. Cl. ...................................................... 607/53
(58) Field of Classification Search ............ 607/53–54, 607/116
See application file for complete search history.

(56) References Cited

U.S. PATENT DOCUMENTS

| | | | |
|---|---|---|---|
| 4,628,933 A * | 12/1986 | Michelson | ................... 607/53 |
| 5,016,633 A | 5/1991 | Chow | |
| 5,024,223 A | 6/1991 | Chow | |
| 5,397,350 A | 3/1995 | Chow et al. | |
| 5,556,423 A * | 9/1996 | Chow et al. | ................ 623/6.63 |
| 5,836,996 A | 11/1998 | Doorish | |
| 5,865,839 A | 2/1999 | Doorish | |
| 5,935,155 A * | 8/1999 | Humayun et al. | ............. 607/54 |
| 2002/0091421 A1* | 7/2002 | Greenberg et al. | ............. 607/54 |

FOREIGN PATENT DOCUMENTS

| | | |
|---|---|---|
| EP | 0 460320 | 1/1998 |
| JP | 8-511697 | 12/1996 |

* cited by examiner

*Primary Examiner*—Mark Bockelman
(74) *Attorney, Agent, or Firm*—Burr & Brown

(57) ABSTRACT

An object is to provide an electrode member for retina stimulation which can form an actually transmitted image without pressing the retina in an excessively broad range and to provide an artificial retina device using the electrode member. An electrode member includes electrodes disposed in a shape of a vertical and horizontal matrix, a support holding each electrode at a predetermined position, and a fixing pin fixing four corners of the support to a sclera. Each electrode projects in the shape of a needle from an opposed face of the support toward a retina. The fixing pin is provided with a positioning projection allowing a distal end of each electrode to come into contact with retinal bipolar cells and limiting the overall opposed face to come into contact with a retina when the support is fixed to the retina.

13 Claims, 9 Drawing Sheets

US 7,158,836 B2

ELECTRODE MEMBER FOR RETINAL STIMULATION, AND ARTIFICIAL RETINAL DEVICE USING THE ELECTRODE MEMBER

TECHNICAL FIELD

The present invention relates to an electrode member for retinal stimulation, and an artificial retina device or the like using the electrode member.

DESCRIPTION OF BACKGROUND ART

No effective cure has yet been found for loss of sight in spite of recent development in medical technique. Loss of sight is not only a mere obliteration of visual function but also it affects a patient's spiritual life and social life. Accordingly, a technique for curing the loss of sight has been desired.

FIG. 1 is a sectional view of a retina. A sclera A forming an outer layer of an eyeball is outside a retina. Inside the sclera are photoreceptors B, retinal bipolar cells C and retinal ganglion cells D sequentially in this order. Of these, the photoreceptors B serve to receive light and convert it to an electric signal. The retinal bipolar cells C and retinal ganglion cells D serve to transmit the electric signal to the brain. Light incident in front of the eyeball (from downward in the figure) passes through the transparent retinal ganglion cells D and retinal bipolar cells C to be sensed by the photoreceptors B and converted to an electric signal. Thereafter, the electric signal is transmitted through the retinal bipolar cells C to the retinal ganglion cells D. Distal ends of the retinal ganglion cells D extend into the brain, and the electric signal forms an image in the brain.

FIG. 2 is a sectional view of a conventional electrode member for retinal stimulation 100 (hereinafter referred to as "electrode member 100") attached over a retina. The electrode member 100 is connected to one end of an electric wire 104 there to transmit, to the retinal bipolar cells C, an electric signal for an image transferred from the other end (not shown) of the electric wire. The electrode member 100 is provided with a plurality of electrodes 101 transmitting an electric signal, a support 102 holding the electrodes 101 at a predetermined location (for example, in a matrix) and a fixing pin 103 for fixing the support 102 to the sclera A. Each electrode 101 is provided so as to be exposed flat on the underside (side in contact with the retina) of the support 102.

However, when the fixing pin 103 is inserted into the sclera A so that the electrode member 100 is fixed over the retina, the support 102 is sometimes depressed against the retina more than necessary. In this case, since the electrode member 100 is fixed over the retina while the overall underside of the support 102 is in contact with the retina, there is a possibility that the underside of the support may press the retina, adversely affecting the retina.

Furthermore, although a portion to which the electrode 101 originally supplies the electric signal is the retinal bipolar cells C, the conventional electrode member 100 has such a structure that the electric signal is also supplied to the retinal ganglion cells D as well. The retinal ganglion cells D extend into the shape of a stalk in order to transmit electric signals from a plurality of the retinal bipolar cells C. Accordingly, for example, as shown in FIG. 3, even when voltage corresponding to an image of character "H" (voltage is applied to the electrodes 101 indicated by "+") is applied in the case of the electrode member 100 provided with 36 electrodes 101, the user (a sightless person) sometimes recognizes it as an image of character "U."

The present invention was made in view of the foregoing circumstances, and an object thereof is to provide an electrode member for retinal stimulation which can form an actually transmitted image without pressing the retina in an excessively broad range.

Furthermore, another object is to provide an artificial retina device which can transmit an image signal into the brain using the electrode member.

DISCLOSURE OF THE INVENTION

To solve the above-noted problem, a first invention is an electrode member for retinal stimulation, provided with a plurality of electrodes transmitting electric signals to a retina and a support holding the electrodes at predetermined positions, characterized in that the support has an opposed face opposed to the retina and provided with a positioning projection.

The retina means a sensory nerve epithelium located at an innermost of the eyeball and includes photoreceptors, retinal bipolar cells and retinal ganglion cells throughout the specification.

The positioning projection is provided so as to project from the opposed face of the support toward the retina side throughout the specification. Furthermore, a position where the positioning projection is provided is not necessarily located inside the support and may be provided at a position projecting at one side of the support. Furthermore, the number of the positioning projections may be one or more. Furthermore, a plurality of electrodes may be disposed only in the center of the support and the other portion of the support may serve as the positioning projection.

According to the first invention, the positioning projection of the support comes into contact with the retina when the electrode member for retinal stimulation is attached over the retina. Consequently, the effect of press against a part of the retina stimulated by the electrode can be reduced as compared with the case where the overall underside of the support comes into contact with the retina as in the prior art.

A second invention is characterized in that in the electrode member for retinal stimulation of the first invention, the positioning projection additionally serves as a fixing portion fixing the support onto the retina.

A shape of the electrode does not matter in the first and second inventions, and for example, it may be a conventional sheet electrode coming into contact with the retinal ganglion cells or a needle-shaped electrode.

Throughout the specification, the fixing portion means a part fixing the support of the electrode member for retinal stimulation at a predetermined position on the retina and includes (a) one provided on the support to give fixation due to attraction between the support and the retina, or (b) one discrete from the support to press the support against the retina thereby to fix the electrode member. As the construction included in (a) are exemplified a pin reaching the sclera, adhesive agent, thread joining by stitching the support and the retina or the like. As the construction included in (b) is exemplified a member pressing a front hemisphere within an eyeball thereby to fix the support.

"Additionally serving" includes, for example, (1) the case where the physically identical construction serves both as the positioning projection and the fixing portion, such as fixing a distal end of the positioning projection (a face contacting with the retina) to the retinal using an adhesive agent or thread, and (2) the case where a part of the fixing portion serves as a positioning projection, for example, a proximal end of the pin serving as the fixing portion is formed with a stepped portion so as to be thickened so that the stepped portion serves as a positioning projection coming into contact with the retina.

According to the second invention, since a single construction serves both as the positioning projection and as the fixing portion, the construction of the electrode member for retinal stimulation can be simplified as compared with the case where both are provided so as to project individually.

A third invention is an electrode member for retinal stimulation, provided with a plurality of electrodes transmitting electric signals to a retina and a support holding the electrodes at predetermined positions, characterized in that each electrode projects from an opposed face of the support opposed to the retina into a shape of a needle with a height reaching a retinal ganglionic layers of the retina.

Each electrode necessitates at least such a height as to reach the retinal bipolar cells from the surface side of the retina (the side of the retinal ganglion cells). Since the height is expected to differ from one sightless person to another, the height is preferably measured previously for each actual patient. Thus, the height of each electrode cannot be defined unconditionally, but generally ranges from about 100 μm to about 300 μm.

According to the third invention, each electrode supplying the electric signal is formed into the needle shape with a predetermined height and the electrode member is attached to the retina so that each electrode is brought into direct contact with the retinal bipolar cells. Accordingly, an image more approximated to an actual one can be formed as compared with the conventional case where the electric signal is applied via the retinal ganglion cells to the retinal bipolar cells.

A fourth invention is characterized in that in the electrode member for retinal stimulation of the first or second invention, each electrode projects from an opposed face of the support opposed to the retina into a shape of a needle with a height reaching a retinal ganglionic layers of the retina.

According to the fourth invention, an adverse effect of pressing the retina can be reduced since the positioning projection is provided. Furthermore, an image more approximate to an actual one can be formed since the needle-shaped electrodes transmit the electric signals directly to the retinal bipolar cells.

A fifth invention is characterized in that in the invention of each of claims 3 and 4, each electrode is covered with an insulator in an overall periphery except a distal end thereof.

The phrase, "except a distal end thereof" means that the electrode member is arranged so that the electric signal each electrode applies stimulates only the targeted retinal bipolar cells and does not stimulate other cells.

According to the fifth invention, an image more approximate to an actual one can be formed since the electric signal tends to be applied only to the retinal bipolar cells.

A sixth invention is characterized in that in the invention of each of claims 3 to 5, the opposed face of the support is provided with a ground electrode.

The ground electrode may be provided on a part of the opposed face of the support or the overall opposed face of the support.

When a sheet electrode is provided on the opposed face of the support, a ground electrode cannot be brought into contact with the retina and is accordingly provided on a portion different from an eyeball. According to the sixth invention, however, the ground electrode can be provided so as to be in contact with the retina since the electrode is formed into the needle shape and inserted into the retina.

A seventh invention is a method of retinal stimulation, characterized by applying a first stimulating voltage to electrodes corresponding to a predetermined image pattern among a plurality of electrodes for retinal stimulation disposed in a matrix shape, and applying a second stimulating voltage to electrodes corresponding to a background region of the image pattern, the second stimulating voltage having a reversed polarity to the first stimulating voltage relative to a ground polarity.

An eighth invention is an artificial retina device characterized by the electrode member for retinal stimulation described in any one of claims 1 to 6, a fixing portion fixing the electrode member onto a retina and a signal transmission section transmitting an image forming electric signal to the electrode.

The signal transmission section transmits an electric signal to an electrode. The signal transmission section can be provided outside the eyeball and connected to an electric wire extending from the electrode. However, the signal transmission section is preferably provided integrally with the electrode member for retinal stimulation and implanted in the eyeball. In this case, a signal transmitting circuit is preferably provided on an outer body of the user so that the electric signal is transmitted by a wireless system (for example, electric wave, optical signal).

According to the eighth invention, the electric signal transferred from the signal transmission section is transmitted via the electrode to the retinal ganglion cells to be formed into an image within the brain.

A ninth invention is an artificial retina device comprising an electrode member for retinal stimulation, provided with a plurality of electrodes transmitting electric signals to a retina and a support holding the electrodes at predetermined positions, a fixing portion fixing the electrode member onto the retina and a signal transmission section transmitting an image forming electric signal to the electrode, characterized in that said plurality of the electrodes are disposed in a matrix shape, a first stimulating voltage is applied to the electrodes corresponding to a predetermined image pattern among said plurality of the electrodes, and a second stimulating voltage is applied to the electrodes corresponding to a background region of the image pattern, the second stimulating voltage having a reversed polarity to the first stimulating voltage relative to a ground polarity.

Furthermore, a tenth invention is an artificial retina device comprising the electrode member for retinal stimulation described in any one of claims 1 to 6, a fixing portion fixing the electrode member onto a retina and a signal transmission section transmitting an image forming electric signal to the electrode, characterized in that said plurality of the electrodes are disposed in a matrix shape, a first stimulating voltage is applied to the electrodes corresponding to a predetermined image pattern among said plurality of the electrodes, and a second stimulating voltage is applied to the electrodes corresponding to a background region of the image pattern, the second stimulating voltage having a reversed polarity to the first stimulating voltage relative to a ground polarity.

It is known that a retinal bipolar cell includes an ON-type which transmits positive voltage pulses to retinal ganglion cells in response to light stimulus to the photoreceptor and an OFF-type which transmits negative voltage pulses to retinal ganglion cells. In conventional artificial retina devices, a stimulating voltage is applied to only one or more of a plurality of electrodes corresponding to an image pattern. Accordingly, it is difficult to achieve a sufficient contrast with respect to the image pattern.

In each of the seventh, ninth and tenth inventions, the first and second stimulating voltages are applied in view of the ON-type and OFF-type bipolar cells. The first stimulating voltage corresponds to an image pattern and the second stimulating voltage corresponds to a background region of the image pattern and has a reversed polarity to the first stimulating voltage relative to a ground polarity. Consequently, a sufficient contrast can be given to the image pattern formed in the brain.

An eleventh invention is characterized in that in the tenth invention, a control device is provided for controlling the image forming electric signal, and the fixing portion serves as a coil capable of supplying a power source to the control device.

When the signal transmission section and the electrode member are attached in the eyeball, it is preferable to transmit a signal from outside the eyeball to the signal transmission section by radio transmission. In such an arrangement, a control device (for example, a microcomputer) controlling the electric signal is preferably provided between the signal transmission section and the electrode member. In this case, however, it is difficult to supply electric power to the control device. Accordingly, the fixing portion is arranged to also serve as a coil in the present invention so that an induction current is induced in the coil, whereby electric power can be supplied to the control device.

A twelfth invention is an operating method characterized by forming an opening by opening a front of an eyeball and inserting an artificial retina device into an inside of the eyeball. Furthermore, the artificial retina device is preferably described in any one of claims 8 to 11.

Tissues (for example, cornea) in the front of the eyeball are not necessarily left for a person undergoing an operation for implanting in an eyeball the artificial retina device described in each of the eighth to eleventh inventions. Accordingly, the front of the eyeball can be opened so that an opening is formed. In this surgical manner, the artificial retina device can easily be inserted.

In the figures, 1 . . . electrode member for retinal stimulation, 2 . . . electrode, 3 . . . support, 3A . . . opposed face, 4, 23 . . . fixing portion, 5 . . . positioning projection, 6 . . . ground electrode, 7, 11, 21 . . . signal transmission section, 22 . . . control device, 8, 10, 20 . . . artificial retina device, C . . . retina bipolar cell, and F . . . retina.

BEST MODE FOR ENFORCING THE INVENTION

Several embodiments of the present invention will be described with reference to the accompanying drawings. However, the technical scope of the invention should not be limited by the following description of the embodiments but may be modified without departing the gist. Furthermore, the technical scope of the present invention should cover a scope of equivalence.

First Embodiment

Figure 1:
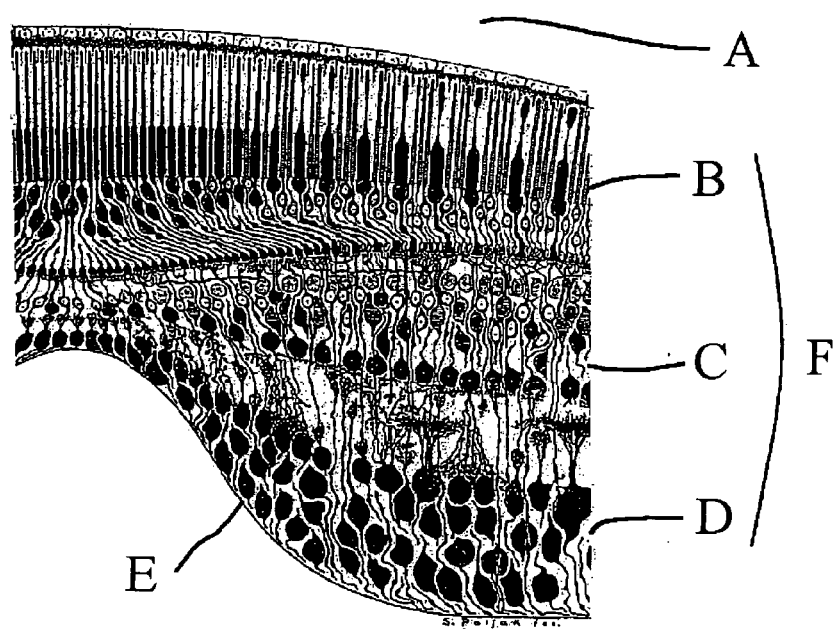
FIG. 1 is a side sectional view of a retina.
Figure 2:
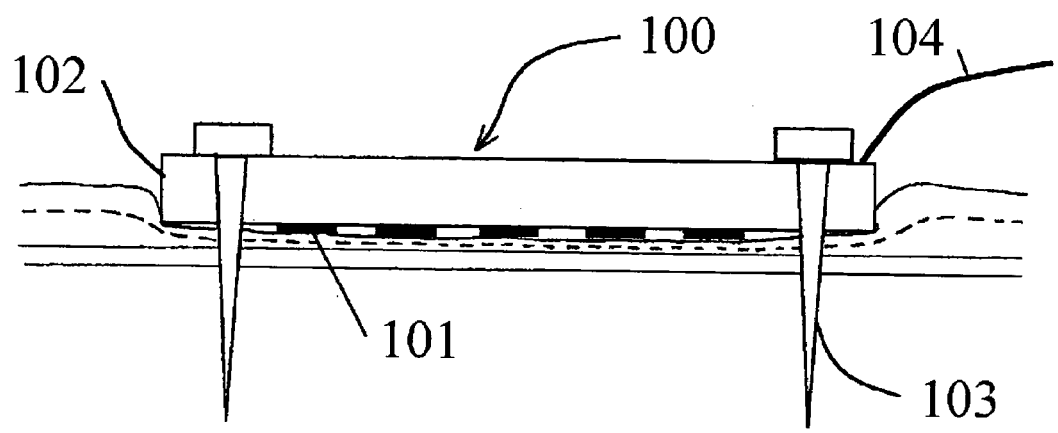
FIG. 2 is a side sectional view of a retina to which a conventional example of electrode member for retinal stimulation is attached.
Figure 3:
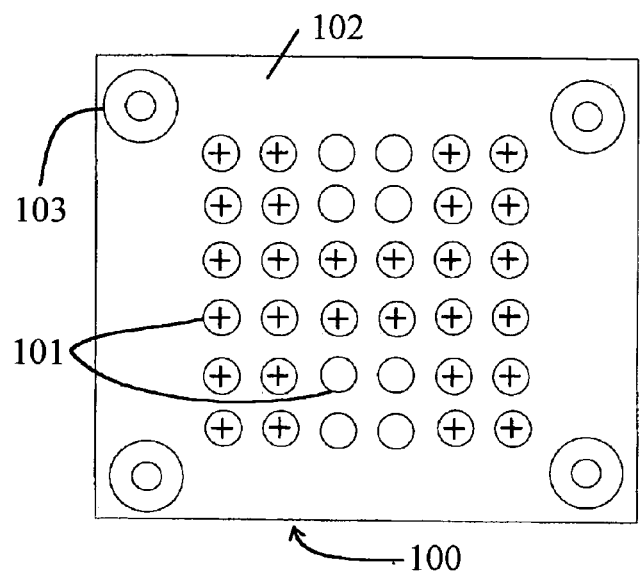
FIG. 3 illustrates a manner of applying a stimulating voltage to a plurality of electrodes in the conventional example.

A first embodiment will be described with reference to FIGS. 1 to 8. FIG. 1 is a side sectional view of a retina F of a healthy person. The sclera A is located outside the retina F and covers an outer face of the eyeball. Inside the sclera A are photoreceptors B, retinal bipolar cells C and retinal ganglion cells D sequentially in this order. The electrode member 1 for retinal stimulation of the embodiment (hereinafter referred to as "electrode member 1") is expected to be applied to patients of Retinitis Pigmentosa and age-related macular degeneration (ARMD). In symptoms of these patients, photoreceptors B are degenerated such that light cannot be converted to electric signals. Next, a visual path such as the retinal bipolar cells C and retinal ganglion cells D fails to function, which failure results in loss of sight. However, it is known that about 70% of the retinal bipolar cells C and about 30% of the retinal ganglion cells D are left in a patient heavily suffered from Retinitis Pigmentosa. The electrode member 1 is mounted at the retinal ganglion cells D side to directly transmit electric signals to retinal bipolar cells C.

Figure 4:
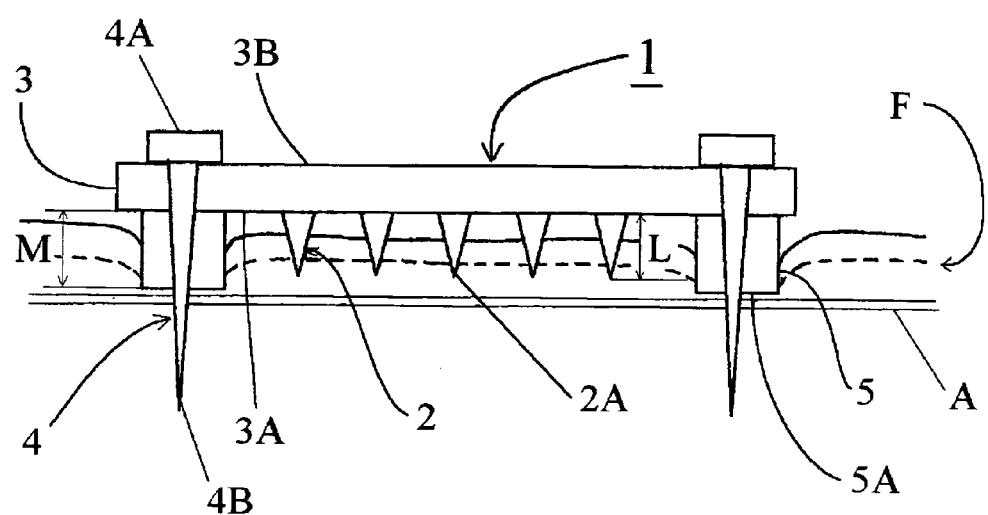
FIG. 4 is a side sectional view of a retina to which a first embodiment of electrode member for retinal stimulation is attached.

The description will go forward with reference to FIGS. 4 to 7. FIG. 4 shows the electrode member 1 attached to the retina. The electrode member 1 comprises a plurality of electrodes 2 transmitting electric signals to the retina F, a support 3 holding the electrodes 2 in a shape of a vertical and horizontal matrix, and a fixing pin 4 (corresponding to a fixing portion in the invention) fixing the support 3 to the retina. The support 3 is made of an insulating resin (for example, Kepton manufactured by CHOMERICS CO.) into the shape of a generally rectangular thin plate. As shown in an enlarged form in FIG. 5, electrodes 2 are disposed at respective predetermined positions inside the support 3. Each electrode 2 (which can be made from iridium, for example) projects in the shape of a needle from an opposed face 3A of the support 3 opposed to the retina F (lower in FIG. 5). Each electrode 2 has a height L starting from the opposed face 3A and set to extend from the surface E of the retina to the retinal bipolar cells C. Furthermore, each electrode 2 is covered with an insulating resin over its entire periphery except for its distal end 2A.

Four corners of the support 3 are provided with respective fixing pins 4 having distal ends 4B projecting from the opposed face 3A. Each fixing pin 4 is made from a ceramic, for example, and has a rear end pressing portion 4A projecting at a top 3B side of the support 3. Each pressing portion 4A is formed into the shape of a disc and pressed when the distal end 4B side of the fixing pin 4 is forced into the sclera A. Each fixing pin 4 has a positioning projection 5 fitted with the distal end 4B side thereof.

Each positioning projection 5 is made from a synthetic resin and formed into a generally cylindrical shape and has an inner diameter slightly smaller than an outer diameter of each fixing pin 4. Each positioning projection 5 has one side bonded to the opposed face 3A. Each positioning projection 5 has a height M which is set to be larger than the height L of each electrode 2 by a predetermined length (as will be described in detail later). A total area of four lower end faces 5A (brought into contact with the retina F) of the positioning projections 5 is set to be smaller than an area of the opposed face 3A.

Figure 5:
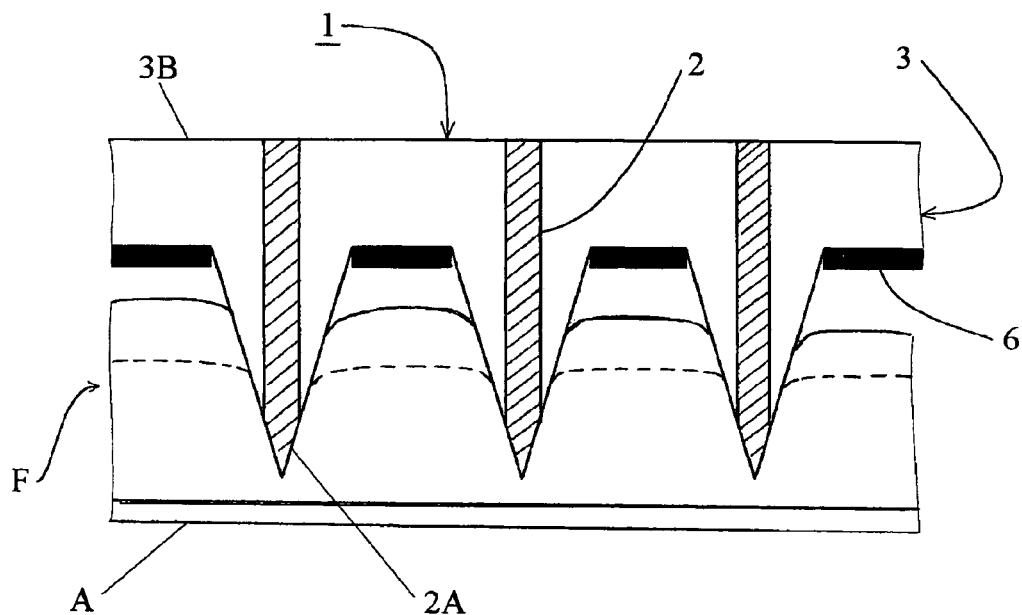
FIG. 5 is an enlarged side sectional view of the retina to which the first embodiment of electrode member for retinal stimulation is attached.

A ground electrode 6 is provided on the parts of the opposed face 3A where no electrodes 2 project, as shown in FIG. 5. The ground electrode 6 is formed as a continuous body and is attached integrally to the opposed face 3 side.

Figure 6:
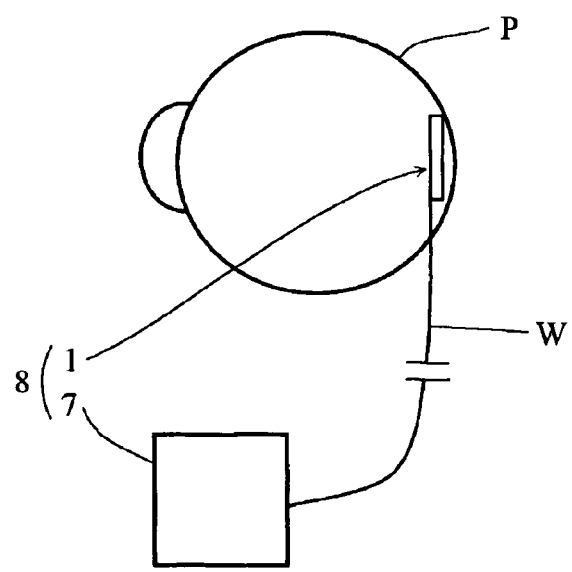
FIG. 6 is a diagram of an artificial retina device of the first embodiment.

In order that the electrode member 1 may be attached to the retina, the overall electrode member 1 is disposed at the predetermined position while the opposed face 3A of the support 3 is being opposed to the retina F. Subsequently, the distal end 4B of the fixing pin 4 is inserted into the retina F, and the pressing portion 4A is further pressed so that the distal end 4B is forced into the sclera A. In this case, the forcing operation progresses while the retina F is sandwiched between the lower end face 5A of the positioning projections 5 and the sclera A. Since the sclera A has a certain strength, it pushes the lower end face 5A back (via the sandwiched retina F) when the pressing portion 4A is pressed to a predetermined depth. Consequently, the fixing pin 4 is found to have been thrust into a predetermined depth. Thus, the lower end face 5A of the positioning projection 5 is positioned. When the electrode member 1 is attached at a predetermined position, the difference (M–L) between the height M of the positioning projection 5 and the height L of the electrode 2 brings the distal ends 2A of the electrodes 2 into contact with the retinal bipolar cells C through the retinal ganglion cells D. Thus, after the electrode member 1 has been attached, electric signals corresponding to an image pattern are transmitted via the electrodes 2 to the retinal bipolar cells C, whereby images can be sent into the brain of the user. As shown in FIG. 6, a signal circuit 7 (corresponding to a signal transmission section in the present invention) is connected via electric wires W extending from the electrodes 2 to the electrode member 1 which is to be attached to the retina in the eyeball. An artificial retina device 8 comprising the signal circuit 7 and the electrode member 1 is attached to the user (or sightless person). The signal circuit 7 is arranged to transmit a predetermined electric signal corresponding to an image to a plurality of electrodes 2. The electric signal is transmitted through the distal end 2A of the electrode 2 to the retinal bipolar cells C.

Figure 7:
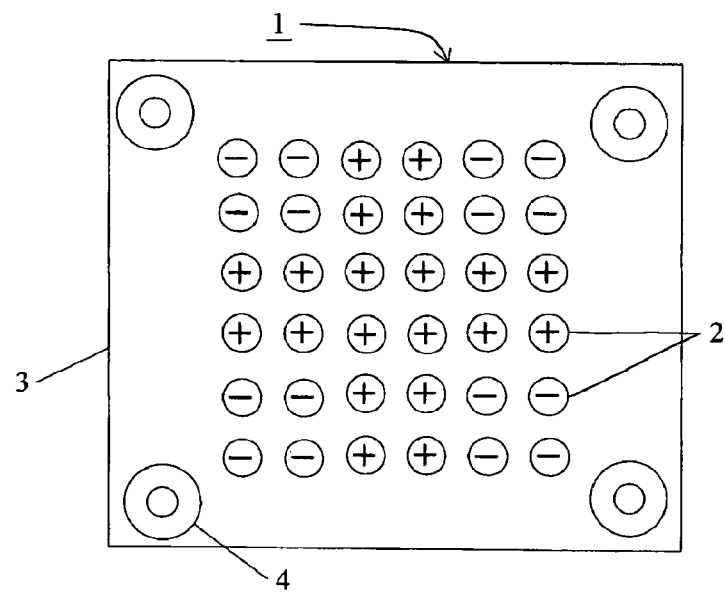
FIG. 7 illustrates a manner of applying a stimulating voltage to a plurality of electrodes in the first embodiment.
Figure 8:
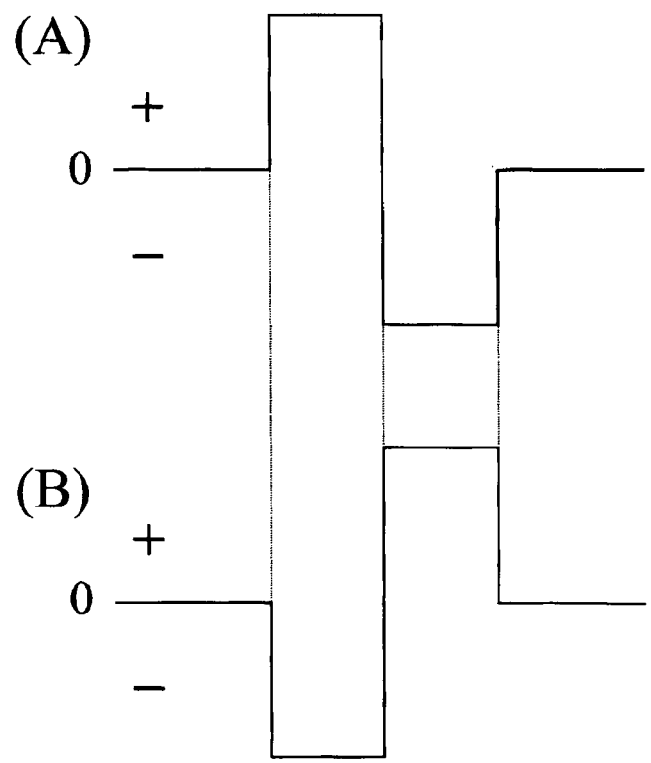
FIG. 8 is a timing chart showing a first stimulating voltage (A) and a second stimulating voltage (B) both applied to a plurality of electrodes in the first embodiment.

A manner of processing the electric signals the signal circuit 7 supplies to a plurality of the electrodes 2 (method of stimulating retina) will be described with reference to FIGS. 7 and 8. FIG. 7 shows the electrode member 1 provided with thirty-six electrodes 2 arranged in the matrix of 6×6. For example, when a generally cross-shaped image pattern is to be transmitted, a first stimulating voltage (FIG. 8A) is applied to the electrodes designated by "+" (or the electrodes corresponding to the cross-shaped image pattern). Furthermore, a second stimulating voltage (FIG. 8B) is applied to the electrodes corresponding to a background region of the cross-shaped image pattern (designated by "−"), the second stimulating voltage having a reverse polarity relative to the ground electrode or first stimulating voltage. Thus, the contrast of image can be improved since the stimulating voltages of both polarities are applied to the electrodes.

According to the embodiment, the positioning projections 5 have the total area brought into contact with the retina F and set to be smaller than the area of the opposed face 3A of the support 3. When the electrode member 1 is attached to the retina, the positioning projections 5 are brought into contact with the retina F. Accordingly, effect of pressure against the retina F can be reduced as compared with the case where the overall underside of the support 102 is brought into contact with the retina F as in the prior art.

Furthermore, each positioning projection 5 also serves as each fixing pin 4. Accordingly, the arrangement of the electrode member 1 can be simplified as compared with a case where each positioning projection and each fixing pin project individually. Additionally, since each fixing pin 4 is brought into contact with the retina F, each fixing pin 4 tends to be subjected to stress. Accordingly, when each positioning projection 5 and each fixing pin 4 are combined together, a part which is most liable to be suffered to stress is fixed, whereupon the overall electrode member 1 can be positioned readily.

Furthermore, each electrode 2 supplying an electric signal is formed into the needle shape and has the predetermined height and is attached to the retina so as to be brought into direct contact with the retinal bipolar cells. Consequently, an image more approximated to an actual one can be formed as compared with the case where the electric signal is applied via the retinal ganglion cells to the retinal bipolar cells as in the conventional electrode 101.

Furthermore, each electrode 2 is covered with the insulator in an overall periphery except a distal end 2A thereof. Consequently, since the electric signal tends to be supplied only to a target, an image more approximated to an actual one can be formed.

Furthermore, since each electrode 2 is formed into the needle shape and inserted into the retina, the ground electrode 6 can be provided so as to be brought into contact with the retina.

Furthermore, in view of the fact that the retinal bipolar cell includes two types of cells, ON-type and OFF-type, the first and second stimulating voltages corresponding to the image pattern and the background region of the image pattern are applied to a plurality of the electrodes 2, the second voltage having a reversed polarity relative to the ground electrode. Consequently, a sufficient contrast can be applied to the image pattern formed in the brain. Furthermore, as a secondary effect, when an image pattern with the same contrast as in the prior art is transmitted (even when an image pattern with finer contrast than in the prior art depending on conditions is transmitted), small current is required such that electrical damage the retina F suffers can be reduced.

Second Embodiment

Figure 9:
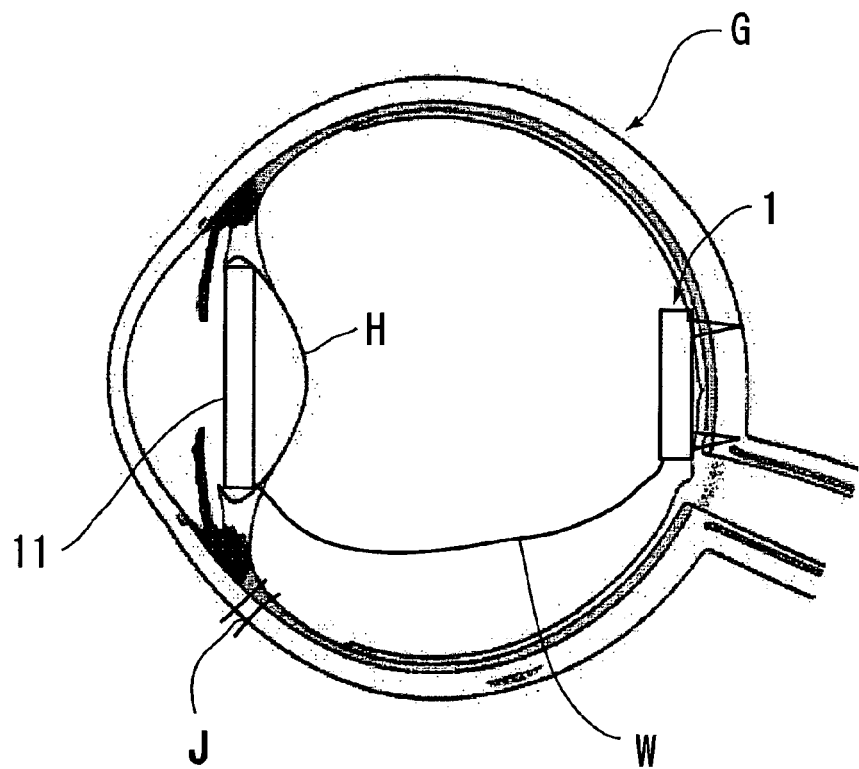
FIG. 9 is a side sectional view of the artificial retina device attached in the eyeball in a second embodiment.

A second embodiment will be described with reference to FIGS. 9 to 11. Firstly, the arrangement of the second embodiment will be described with reference to FIG. 11. The artificial retina device 10 comprises the electrode member 1 and the signal transmitting section 11. Both members 1 and 11 are connected to each other by the electric wire W. The artificial retina device 10 is designed to be attached to an inner part of the eyeball G. The signal transmitting section 11 is a receiver which receives image-forming electric signals from a transmitter 12 provided outside the eyeball G, by a radio system. The signal transmitting section 11 has an outer diameter which ranges from about 5 mm to about 8 mm and is substantially as large as or slightly larger than an inner diameter of a crystal lens H. A signal control device 13 (including for example, a CCD camera, microcomputer, etc.) is connected to the transmitter 12 for generating and controlling image signals.

Figure 10:
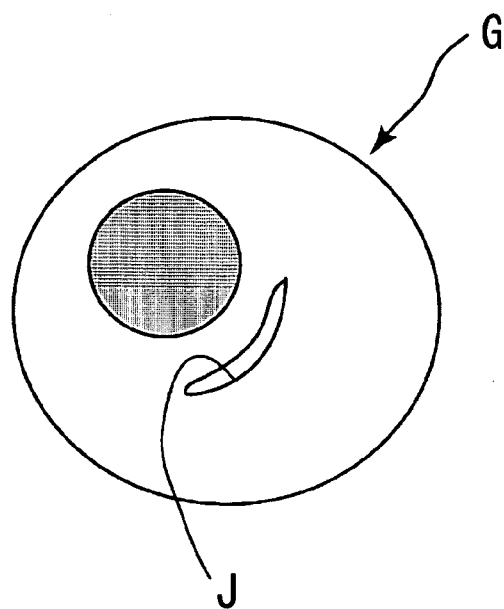
FIG. 10 illustrates a front of the eyeball, showing a degree of incision in the case where the artificial retina device of the second embodiment has been attached in the eyeball.
Figure 11:
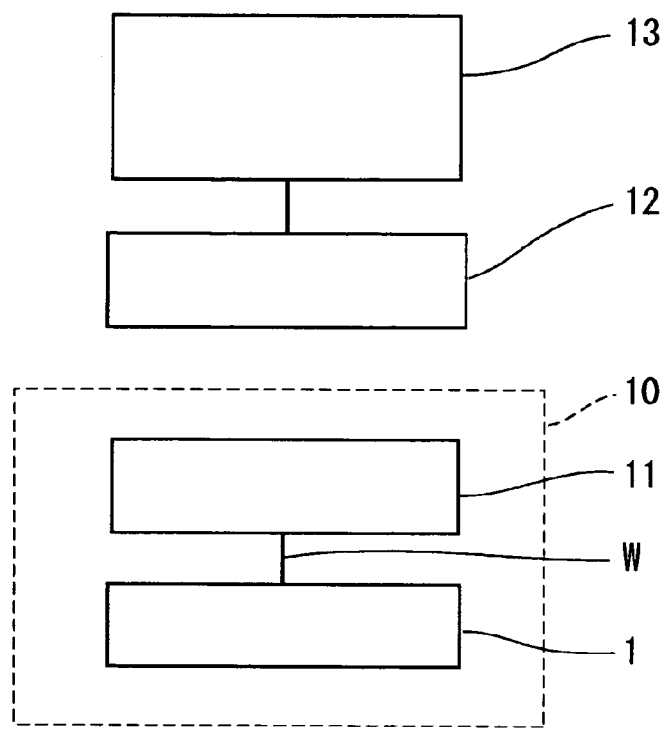
FIG. 11 is a diagram of the artificial retina device of the second embodiment.

In order that the artificial retina device 10 may be attached to the inner part of the eyeball G, the front of the eyeball is cut along an outer periphery of the crystal lens H so that an opening J is formed, as shown in FIG. 10. The electrode member 11 and the signal transmitting section 11 are in turn attached through the opening J into the inner part of the eyeball G.

According to the embodiment, the electric signals from the signal transmitting section 11 are transmitted via the electrodes 2 to the retinal ganglion cells D of the retina F, whereupon an image is formed in the brain.

Third Embodiment

A third embodiment will be described with reference to FIGS. 12 to 16. Firstly, the arrangement of the second embodiment will be described with reference to FIG. 14. The artificial retina device 20 comprises the electrode member 1, the signal transmitting section 21 transmitting electric signals to the electrode member 1, a control device 22 (including a microcomputer) controlling the electric signals and a fixing section 23. The signal transmitting section 21 is a receiver which receives image-forming electric signals from a transmitter 24 provided outside the eyeball G, by a radio system. The control device 22 includes a control circuit 25 and a power supply device 26. The power supply device 26 is a secondary cell such as a lithium cell. The fixing section 23 is provided for fixing the electrode member 1 to the retina (the construction thereof will be described in detail later). The fixing section 23 also serves as a coil to supply to the power supply device 26 a power supply fed by electromagnetic induction from an external primary coil 27. A signal control device 29 (including for example, a CCD camera, microcomputer, etc.) is connected to the transmitter 24 for generating and controlling image signals. The signal control device 29 further controls the primary coil 27.

Figure 14:
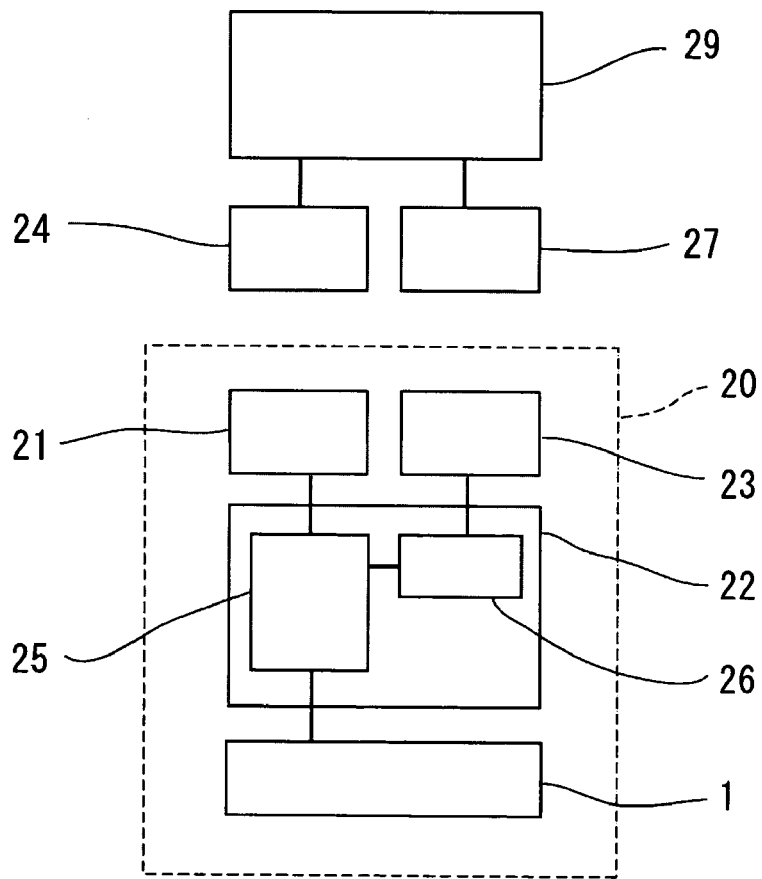
FIG. 14 is a diagram of the artificial retina device of the third embodiment.
Figure 15:
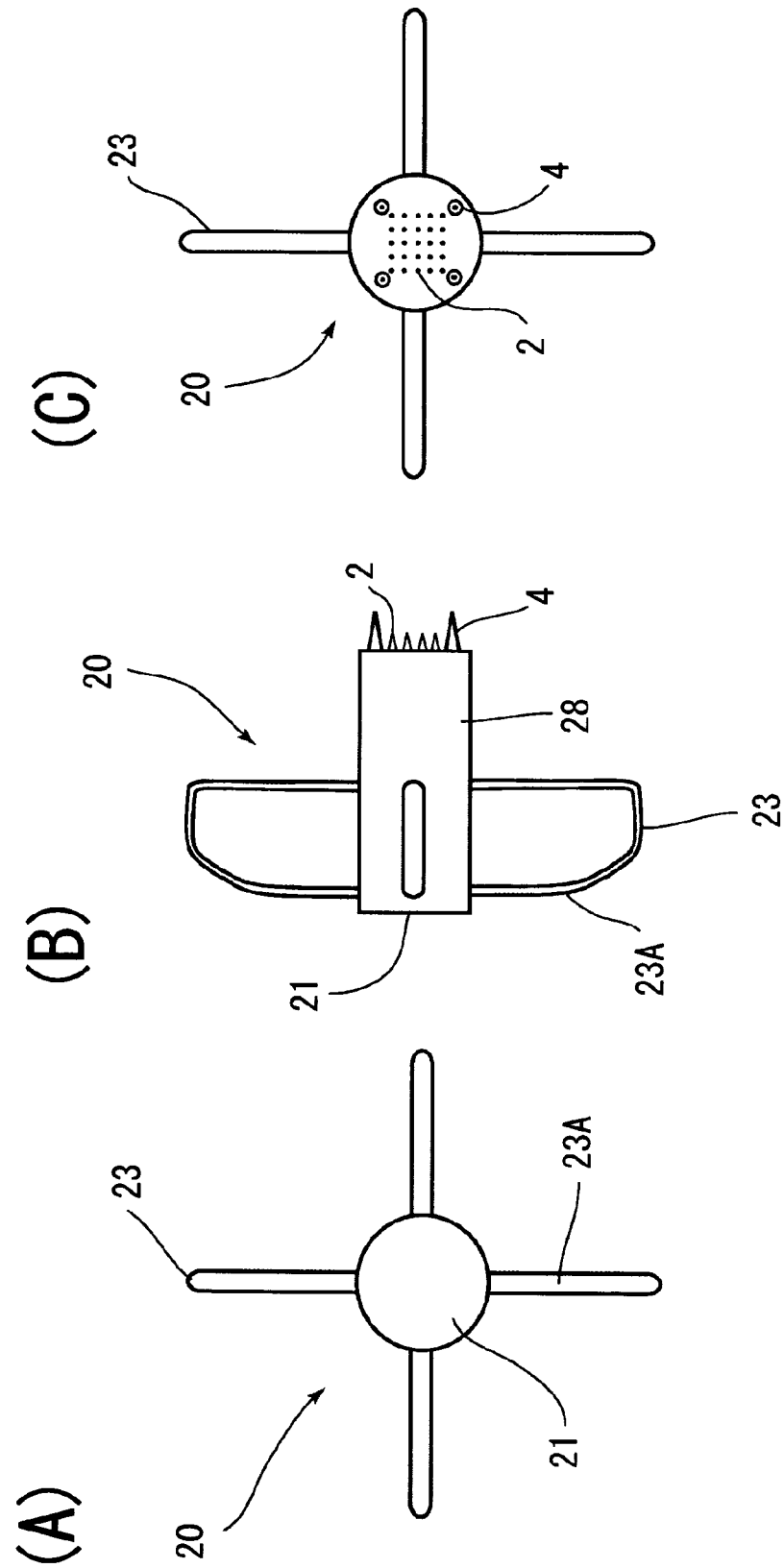
FIG. 15 illustrates appearances of the artificial retina device of the third embodiment having been attached in the eyeball, (A) being a front view, (B) a side view and (C) a rear view.
Figure 16:
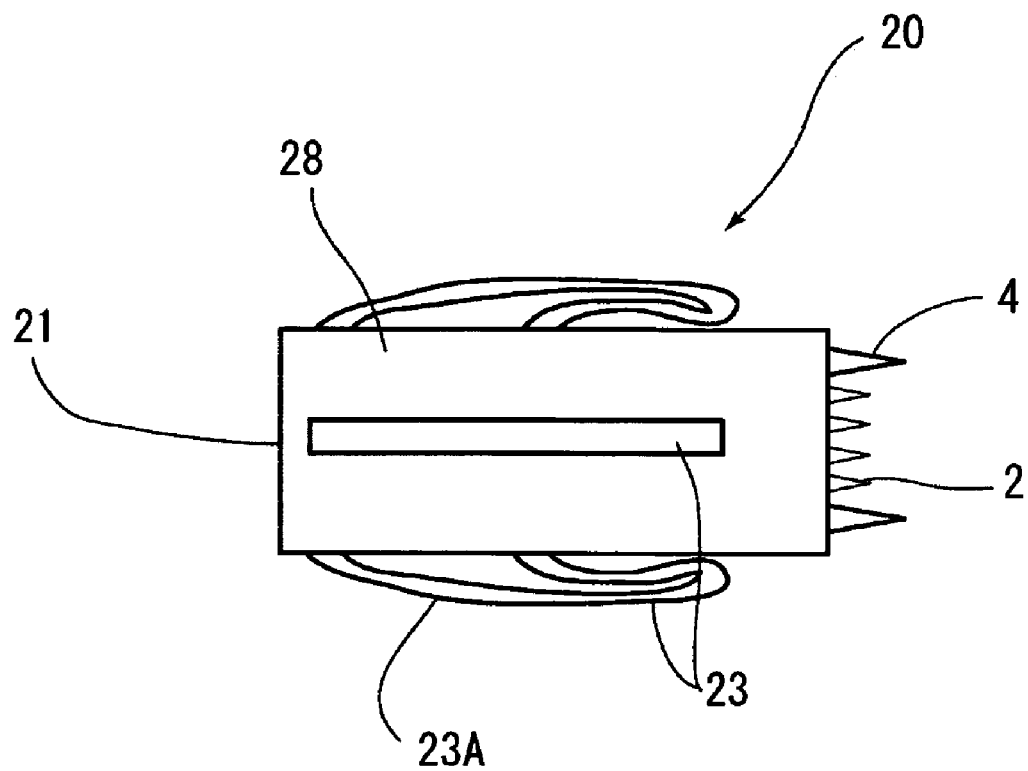
FIG. 16 is a side view of the artificial retina device of the third embodiment before attachment in the eyeball.

The electrode member 1, signal transmitting section 21 and control device 22 are formed integrally into a generally circularly cylindrical body 28 as shown in FIGS. 15 and 16. The cylindrical body 28 is sized so as to be accommodated in the eyeball G as shown in FIG. 14. More specifically, the cylindrical body 28 has a length substantially equal to a length from a yellow spot or retinal fovea to an iris back. The cylindrical body 28 has, at a front of the eyeball Ganouter, diameter slightly smaller than a diameter of a boundary between the sclera and a cornea.

Figure 12:
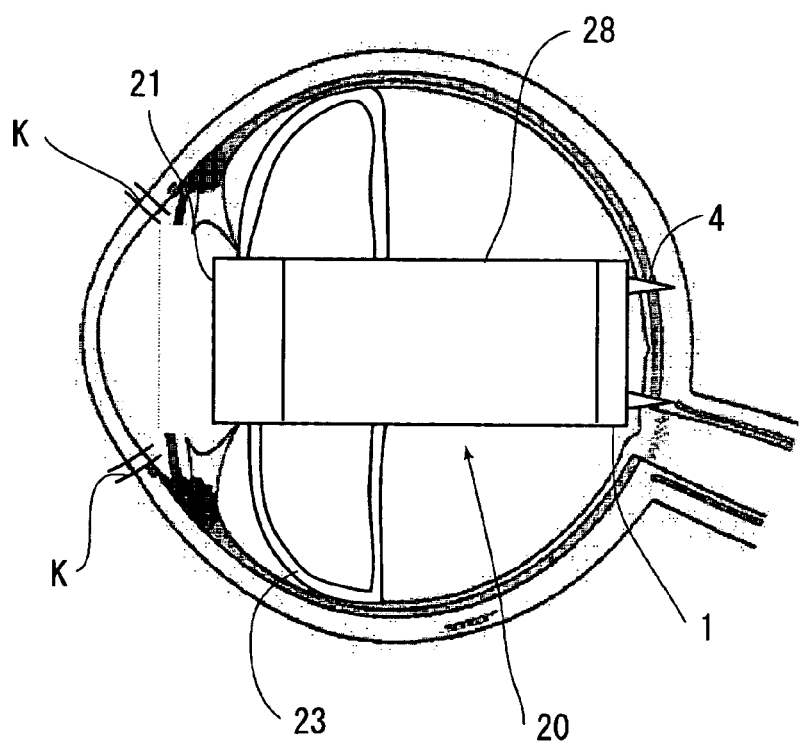
FIG. 12 is a side sectional view of the artificial retina device attached in the eyeball in a third embodiment.

Furthermore, four fixing sections 23 are disposed substantially uniformly along an outer periphery of a front half (a portion located at a front semispherical portion in the eyeball G; and inner face of ciliary body) of the cylindrical body 28. The fixing sections 23 project outward. Each fixing section 23 comprises a member having a suitable resiliency (for example, a shape memory alloy). Both edges of each fixing section 23 are connected to an outer face of the cylindrical body 28 so as to be formed into the shape of a bridge. Each fixing section 23 has a front 23A formed into an arc shape in compliance with an inner wall of the eyeball G. The fixing section 23 is folded along the outer face of the cylindrical body 28 before the artificial retina device 20 is attached inside the eyeball G. On the other hand, after the artificial retina device 20 has been attached inside the eyeball G, the fixing section 23 projects radially with respect to the cylindrical body 28 and is in contact with an inner wall of the front semispherical portion of the eyeball G, as shown in FIGS. 12 and 15. Thus, the fixing section 23 presses the cylindrical body 28 rearward in the eyeball G so that the support 3 of the electrode member 1 is pressed toward the retina F side, whereby the support is fixed at a predetermined position on the retina.

Figure 13:
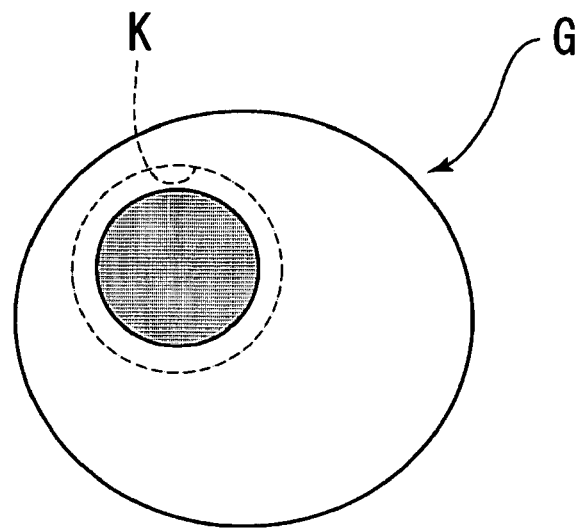
FIG. 13 illustrates a front of the eyeball, showing a degree of incision in the case where the artificial retina device of the third embodiment has been attached in the eyeball.

In order that the artificial retina device 20 constructed as described above may be attached inside the eyeball G, the front of the eyeball is opened so that an opening K is formed, as shown in FIG. 13. The artificial retina device 20 is inserted through the opening K into the inner part of the eyeball G. In a surgical operation for implanting the artificial retina device 20 in the eyeball G, a portion of the eyeball G in the rear of the inner wall portion with which the fixing section 23 is in contact is preferably processed by laser along the inner peripheral face. Even if the fixing section 23 should cause a retinal detachment, it can be arrested from progress toward the retinal fovea as the result of such processing of laser solidification.

According to the embodiment, the fixing section 23 serves as the coil, and the induction current is generated in the coil, whereupon a power supply can be provided for the control device 22.

Furthermore, the artificial retina device can be inserted easily by employing the surgical operation for opening the front of the eyeball G.

The fixing section 23 serves as the coil in the embodiment. However, the fixing section may also serve as an earth, as another modified form. Furthermore, since the fixing section 23 positions the support 3 in the embodiment, the fixing pin 4 for the electrode need not be provided.

The invention claimed is:

1. An electrode member for retinal stimulation comprising:

a plurality of electrodes transmitting electric signals to a retina;

a support holding the electrodes at predetermined positions, the support having an opposed face opposed to the retina, each electrode projecting from the opposed face of the support into a shape of a needle that tapers into a sharp point with a height reaching retinal ganglionic layers of the retina; and positioning projections, each having first and second surfaces, the first surface being attached to the opposed face of the support, the second surface located a distance beyond the height of the electrodes, each positioning projection having a fixing pin located therein extending beyond the second surface of the positioning projections.

2. An electrode member for retinal stimulation according to claim 1, wherein the positioning projection additionally serves as a fixing portion fixing the support onto the retina.

3. An electrode member for retinal stimulation according to claim 1, wherein each electrode is covered with an insulator in an overall periphery except a distal end thereof.

4. An electrode member for retinal stimulation according to claim 1, wherein the opposed face of the support is provided with a ground electrode.

5. An artificial retina device comprising the electrode member for retinal stimulation according to claim 4, said device further comprising a signal transmission section transmitting an image forming electric signal to the electrode.

6. An operating method characterized by forming an opening in a front of an eyeball and inserting the artificial retina device of claim 5 into an inside of the eyeball.

7. An artificial retina device comprising the electrode member for retinal stimulation according to claim 1, said device further comprising a signal transmission section transmitting an image forming electric signal to the electrodes, wherein:
 said plurality of electrodes are disposed in a matrix shape;
 a first stimulating voltage is applied to electrodes corresponding to a predetermined image pattern among said plurality of electrodes; and
 a second stimulating voltage is applied to electrodes corresponding to a background region of the image pattern, the second stimulating voltage having a reversed polarity to the first stimulating voltage relative to a ground polarity.

8. An artificial retina device according to claim 7, further comprising a control device controlling the image forming electric signal, wherein the fixing portion serves as a coil capable of supplying a power source to the control device.

9. An operating method characterized by forming an opening in a front of an eyeball and inserting the artificial retina device of claim 8 into an inside of the eyeball.

10. An operating method characterized by forming an opening in a front of an eyeball and inserting the artificial retina device of claim 7 into an inside of the eyeball.

11. A method of retinal stimulation, comprising the steps of:
 providing a support holding a plurality of electrodes at predetermined positions, each electrode projecting from an opposed face of the support into a shape of a needle that tapers into a sharp point with a height reaching ganglionic layers of the retina;
 providing positioning projections on the opposed face of the support, each positioning projection having first and second surfaces, the first surface being attached to the opposed face of the support, the second surface located a distance beyond the height of the electrodes, each positioning projection having a fixing pin located therein extending beyond the second surface of the positioning projections;
 applying a first stimulating voltage to electrodes corresponding to a predetermined image pattern among the plurality of electrodes for retinal stimulation disposed in a matrix shape; and
 applying a second stimulating voltage to electrodes corresponding to a background region of the image pattern, the second stimulating voltage having a reversed polarity to the first stimulating voltage relative to a ground polarity.

12. An artificial retina device comprising an electrode member for retinal stimulation, said electrode member comprising:
 a plurality of electrodes transmitting electric signals to a retina, each electrode projecting from a support holding the electrodes at predetermined positions and tapering into a sharp point with a height reaching ganglionic layers of the retina;
 positioning projections, each having first and second surfaces, the first surface being attached to the opposed face of the support, the second surface located a distance beyond the height of the electrodes, each positioning projection havin a fixing pin located therein extending beyond the second surface of the positioning projections; and
 a signal transmission section transmitting an image forming electric signal to the electrodes, wherein:
 said plurality of electrodes are disposed in a matrix shape;
 a first stimulating voltage is applied to electrodes corresponding to a predetermined image pattern among said plurality of electrodes; and
 a second stimulating voltage is applied to electrodes corresponding to a background region of the image pattern, the second stimulating voltage having a reversed polarity to the first stimulating voltage relative to a ground polarity.

13. An operating method characterized by forming an opening in a front of an eyeball and inserting the artificial retina device of claim 12 into an inside of the eyeball.

* * * * *